(12) United States Patent
Fisher et al.

(10) Patent No.: US 11,141,285 B2
(45) Date of Patent: Oct. 12, 2021

(54) CARPAL BONE FUSION DEVICE AND METHOD

(71) Applicant: BAYLOR UNIVERSITY, Waco, TX (US)

(72) Inventors: Connor Fisher, New Braunfels, TX (US); Zachary Collins, Colorado Springs, CO (US); Alex Chen, Frisco, TX (US); Chad Regensberg, Apple Valley, CA (US); Tim Adeleye, The Woodlands, TX (US); Joshua Buckner, Dedham, MA (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 16/055,899

(22) Filed: Aug. 6, 2018

(65) Prior Publication Data
US 2020/0038195 A1  Feb. 6, 2020

(51) Int. Cl.
*A61F 2/42* (2006.01)
*A61B 17/064* (2006.01)
*A61B 17/80* (2006.01)
*A61F 2/30* (2006.01)

(52) U.S. Cl.
CPC ........ *A61F 2/4261* (2013.01); *A61B 17/0642* (2013.01); *A61B 17/8014* (2013.01); *A61B 17/8057* (2013.01); *A61B 17/8061* (2013.01); *A61F 2/30749* (2013.01); *A61F 2002/30622* (2013.01); *A61F 2002/4271* (2013.01)

(58) Field of Classification Search
CPC .... A61F 2/4261; A61F 2/4264; A61F 2/4266; A61F 2/4269; A61B 17/0642; A61B 2017/0645; A61B 17/8061
See application file for complete search history.

(56) References Cited

U.S. PATENT DOCUMENTS 5,201,737 A  * 4/1993 Leibinger ............ A61B 17/688
                                                   606/280
5,511,565 A  * 4/1996 Syers ................. A61B 17/8071
                                                   128/859
5,578,036 A  * 11/1996 Stone ................... A61B 17/688
                                                   606/281

(Continued)

FOREIGN PATENT DOCUMENTS

WO        2013036362 A1       3/2013

OTHER PUBLICATIONS

Kontakis, G. M., Pagkalos, J. E., Tosounidis, T. I., Melissas, J., Katonis, P., "Bioabsorable materials in orthopaedics", Acta Orthopaedica Belgica, May 2007, pp. 159-169, vol. 73.

(Continued)

*Primary Examiner* — Matthew J Lawson
(74) *Attorney, Agent, or Firm* — Jackson Walker, LLP

(57) ABSTRACT

The present disclosure provides an orthopedic device and method for carpal fusion that provides bone to bone compression and multiple fixation points to decrease multiple degrees of freedom and motion of carpal bones. The device is biocompatible, resistant to corrosion, and sufficient in mechanical strength. Bone to bone compression and fixation points can be increased by using a first set of fasteners in a peripheral portion of the device to couple through the device into bone structure, and a second set of fasteners in a central portion of the device can be coupled through the device into the bone structure.

13 Claims, 4 Drawing Sheets

(56) References Cited

U.S. PATENT DOCUMENTS

| | | | | |
|---|---|---|---|---|
| 6,179,839 | B1* | 1/2001 | Weiss | A61B 17/1659 606/280 |
| 8,911,445 | B2* | 12/2014 | Rocci | A61B 17/1686 606/86 R |
| 2004/0127901 | A1* | 7/2004 | Huebner | A61B 17/8042 606/281 |
| 2005/0261688 | A1* | 11/2005 | Grady, Jr. | A61B 17/8014 606/286 |
| 2006/0149249 | A1* | 7/2006 | Mathoulin | A61B 17/1615 606/915 |
| 2010/0228299 | A1* | 9/2010 | Zrinski | A61B 17/8014 606/286 |
| 2012/0197261 | A1* | 8/2012 | Rocci | A61B 17/1739 606/96 |
| 2013/0190817 | A1* | 7/2013 | Bouduban | A61B 17/0401 606/232 |
| 2017/0007305 | A1* | 1/2017 | Hollis | A61B 17/8057 |
| 2017/0181779 | A1* | 6/2017 | Leither | A61B 17/8014 |

OTHER PUBLICATIONS

Duckworth, A. D., Jenkins, P., Aitken, S. A., Clement, N. D., Court-Brown, C. M., McQueen, M. M., "Scaphoid fracture epidemiology", The Journal of Trauma and Acute Care Surgery, Feb. 2012, pp. E41-E45, vol. 72, Issue 2.

Trail, I. A., Murali, R., Stanley, J. K., Hayton, M. J., Talwalkar, S., Sreekumar, R., Birch, A., "The Long-Term Outcome of Four-Corner Fusion", Journal of Wrist Surgery, May 2015, pp. 128-133.

Waris, E., Ashammakhi, N., Kaarela, O., Raatikainen, T., Vasenius, J., "Use of Bioabsorbable Osterofixation Devices in the Hand", The Journal of Hand Surgery: British and European Volume, Dec. 2004, pp. 590-598, vol. 29, Issue 6.

Salima, F., International Search Report for International Patent Application No. PCT/US2019/044881, dated Nov. 11, 2019, European Patent Office.

Salima, F., Written Opinion for International Patent Application No. PCT/US2019/044881, dated Nov. 11, 2019, European Patent Office.

* cited by examiner (a) Anterior view of left hand    (b) Posterior view of left hand

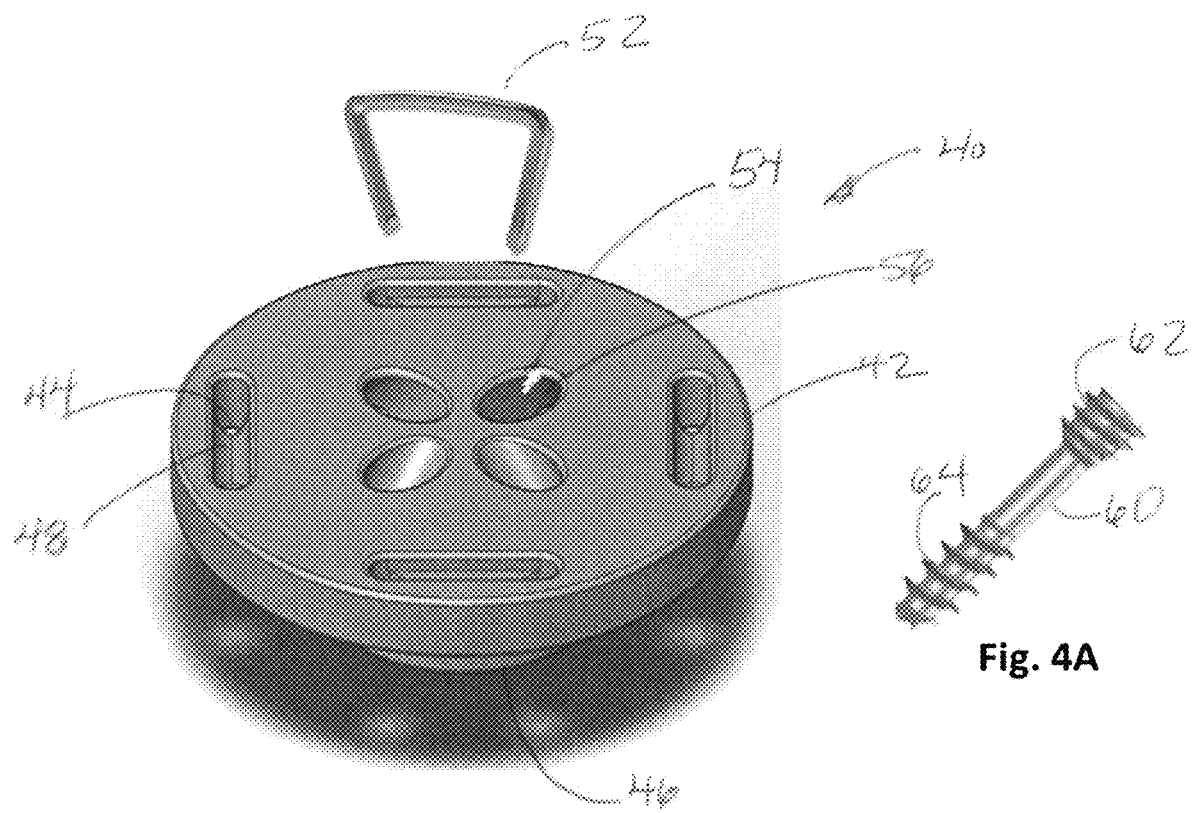
Fig. 4
Fig. 4A
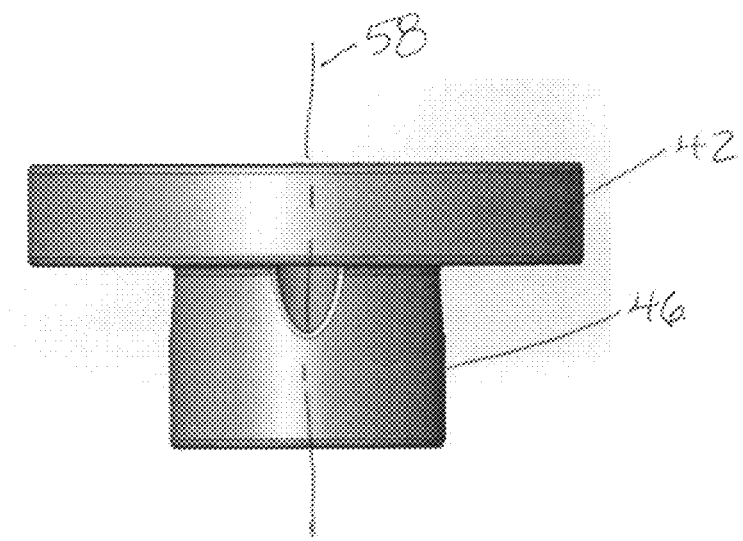
Fig. 5

CARPAL BONE FUSION DEVICE AND METHOD

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates to orthopedic devices and methods. More specifically, the disclosure relates to a orthopedic device and method for fusing of bone structures.

Description of the Related Art

A common injury seen by hand/wrist/elbow orthopedic surgeons is that of the scaphoid fracture, usually as a result of someone trying to catch themselves when they fall forward. Oftentimes, this injury does not heal because the scaphoid does not receive good blood flow. The bone deteriorates and is removed, which causes the wrist to become destabilized. This destabilization is fixed using a salvage procedure, where certain carpal bones (wrist bones) are fused together using for example devices known as four corner fusion devices.

FIG. 1A is an exemplary anterior diagram of a typical bone structure in a hand. FIG. 1B is an exemplary posterior diagram of a typical bone structure in a hand. FIG. 2 is an exemplary diagram of a typical arterial system in a hand. The carpal bones 4 of concern are the scaphoid 6, hamate 8, capitate 10, triquetrum 12, and lunate 14. Carpal bones are only connected by ligaments horizontally. The pisiform 20, triquetrum 12, lunate 14, and scaphoid 6 are only connected by ligaments. The scaphoid 6 also connects to the trapezium 22 and trapezoid 24, which are connected to the capitate 10 and hamate 8 by ligaments. The scaphoid is prone to avascular necrosis, the process where bone dies due to lack of blood supply. Generally, eighty percent (80%) of the blood supply to the scaphoid comes from the superficial palmar branch radial artery 16 and is located at the top of the scaphoid, the remaining twenty percent (20%) is supplied by the dorsal carpal branch radial artery 18, which is also located near the top of the scaphoid. So, when the scaphoid fractures farther away from the area from which the blood supply comes, the scaphoid is more susceptible to avascular necrosis. With the deterioration of the scaphoid, the scaphoid needs to be extracted and the wrist becomes destabilized. The wrist destabilizes, because the scaphoid serves as the link between the two rows of carpal bones.

FIG. 3 is a schematic perspective view of a widely used commercial prior art, four-corner fusion device 30. However, this device and other four-corner fusion methods have roughly a 50% failure rate. The most common failure mechanism is from the single point of fixation in each bone when the bones rotate around screws 32 inserted into the bones, causing loosening and preventing bone fixation. Other issues appear to be: little to no compression strategy (compression promotes bone growth); only one to two fixation points per bone (usually only one depending on patient bone size), which does not prevent motion as well because of multiple degrees of freedom; and a susceptibility to "windshield wiper effect". In the windshield-wiper effect, the screws move within the soft inner, cancellous bone tissue due to different torsional, bending, and axial loads that the device experiences. This movement of the screws prevents the fixation of the carpal bones necessary for fusion to occur and the device and intended fusion may fail.

Therefore, there remains a need for an improved orthopedic device and method that can more effectively stabilize the bones, particularly the carpal bones, to allow them to fuse properly.

BRIEF SUMMARY OF THE INVENTION

The present disclosure provides an orthopedic device and method for carpal fusion that provides bone to bone compression and multiple fixation points to decrease multiple degrees of freedom and motion of carpal bones. The device is biocompatible, resistant to corrosion, and sufficient in mechanical strength. Bone to bone compression and fixation points can be increased by using a first set of fasteners in a peripheral portion of the device to couple through the device into bone structure, and a second set of fasteners in a central portion of the device can be coupled through the device into the bone structure.

The disclosure provides an orthopedic device, comprising: a plate formed with a first set of openings located peripherally around the plate and formed through the plate and a second set of openings located centrally on the plate and formed through the plate at an angle to a longitudinal axis of the plate.

The disclosure provides a method of coupling an orthopedic device to a plurality of bones, the device having a plate formed with a first set of openings located peripherally around the plate and formed through the plate and a second set of a plurality of openings located centrally on the plate and formed through the plate at an angle to a longitudinal axis of the plate, the method comprising: locating the plate adjacent the bones; forming holes in the bones; inserting a first set of fasteners through the peripherally located openings and into the bones; inserting a second set of fasteners through the centrally located openings and into the bones; pulling the bones toward a longitudinal axis of the plate; and at least partially securing the bones toward a longitudinal axis of the plate with second set of fasteners.

BRIEF DESCRIPTION OF THE SEVERAL VIEWS OF THE DRAWINGS

FIG. 4 is a top perspective schematic view of an exemplary orthopedic device of the present disclosure.

FIG. 4A is a perspective schematic view of an exemplary fastener for the device.

FIG. 5 is a side schematic view of the exemplary device shown in FIG. 4.

DETAILED DESCRIPTION

Figures 1A, 1B:
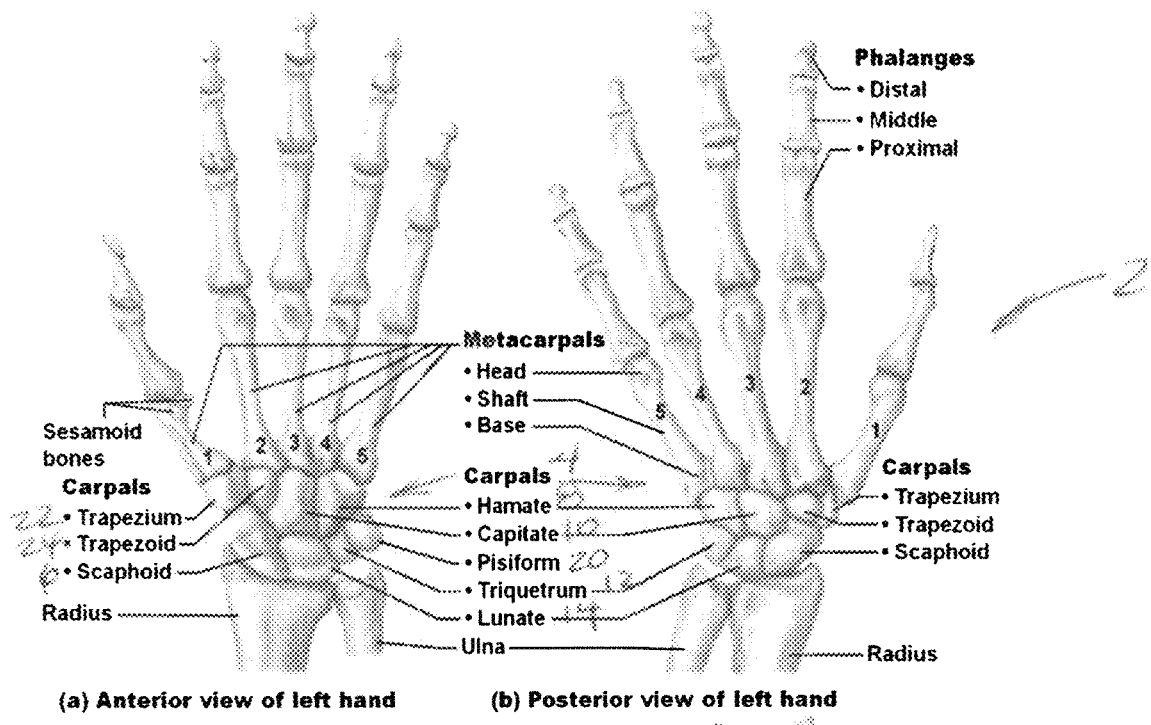
FIG. 1A is an exemplary anterior diagram of a typical bone structure in a hand.
FIG. 1B is an exemplary posterior diagram of a typical bone structure in a hand.
Figure 2:
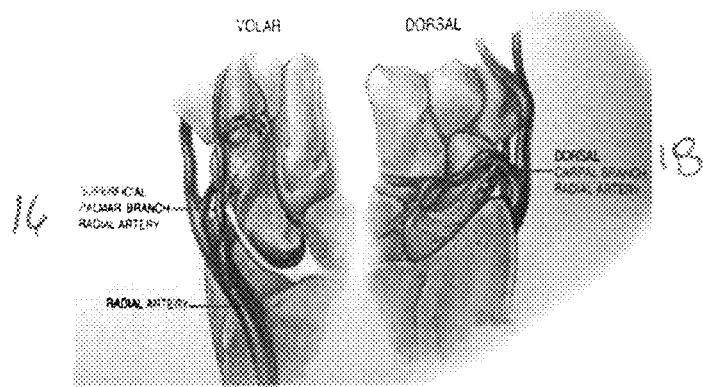
FIG. 2 is an exemplary diagram of a typical arterial system in a hand.

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation or location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Some elements are nominated by a device name for simplicity and would be understood to include a system or a section, such as a processor would encompass a processing system of related components that are known to those with ordinary skill in the art and may not be specifically described.

The present disclosure provides an orthopedic device and method for carpal fusion that provides bone to bone compression and multiple fixation points to decrease multiple degrees of freedom and motion of carpal bones. The device is biocompatible, resistant to corrosion, and sufficient in mechanical strength. Bone to bone compression and fixation points can be increased by using a first set of fasteners in a peripheral portion of the device to couple through the device into bone structure, and a second set of fasteners in a central portion of the device can be coupled through the device into the bone structure. The first set of fasteners can be staples and can be installed into the bone before the second set of fasteners. The second set of fasteners can be a threaded connection with different pitch threads on one end compared to the other end, so that as the fastener is turned, the bone is pulled to the plate and compressed against other bones.

Figure 3:
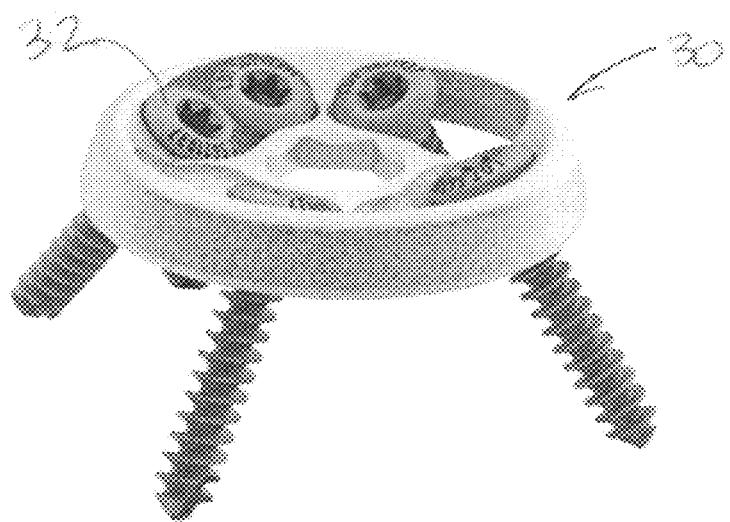
FIG. 3 is a schematic perspective view of a widely used commercial prior art, four-corner, fusion device.

Some advantageous design considerations can be: biocompatible material, limited motion to less than 1 mm in any direction to allow bone fusion, withstands forces of at least that of the carpal bones' maximum capacity, and minimal windshield wiper effect compared to the prior art device illustrated in FIG. 3.

Figure 6:
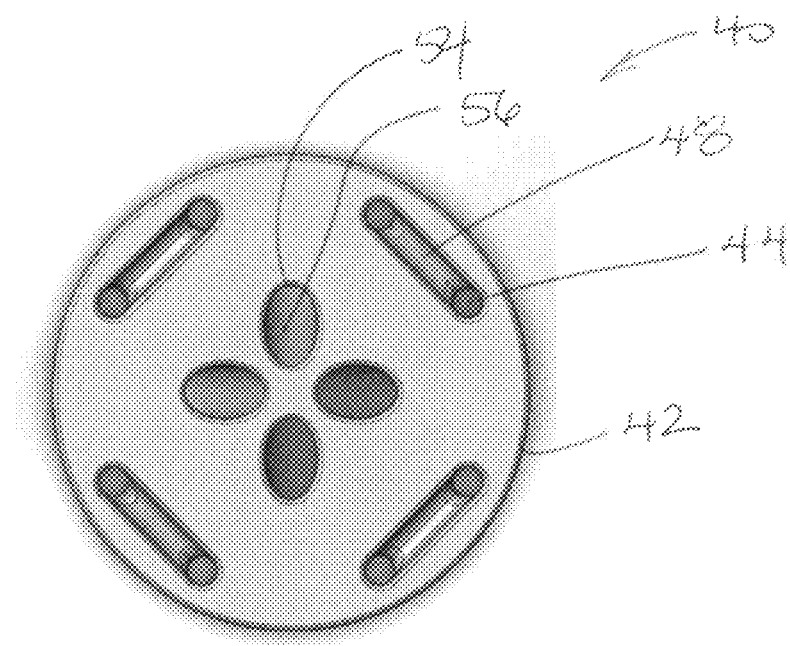
FIG. 6 is a top schematic view of the exemplary device shown in FIG. 4.
Figure 7:
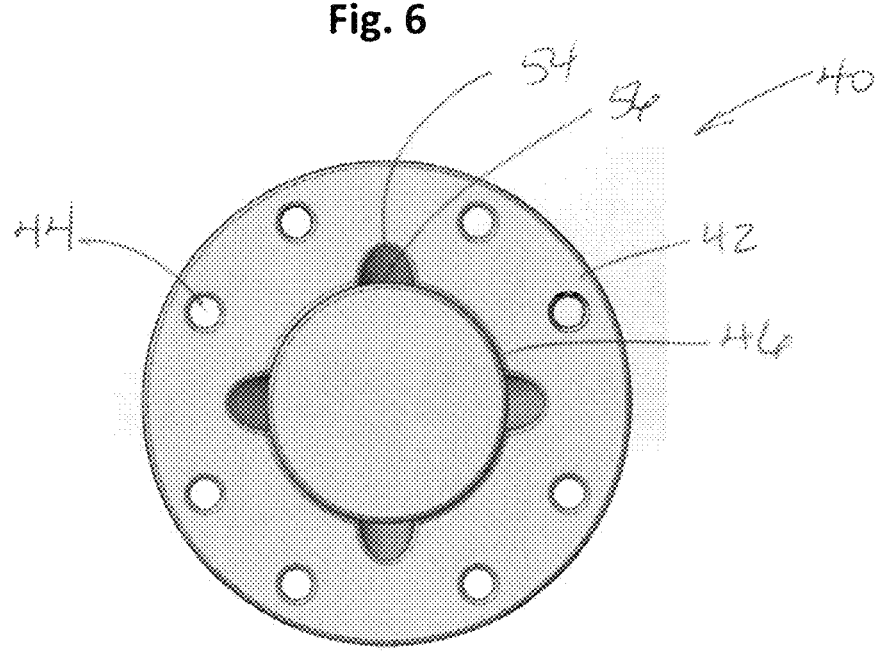
FIG. 7 is a bottom schematic view of the exemplary device shown in FIG. 4.
Figure 1A:
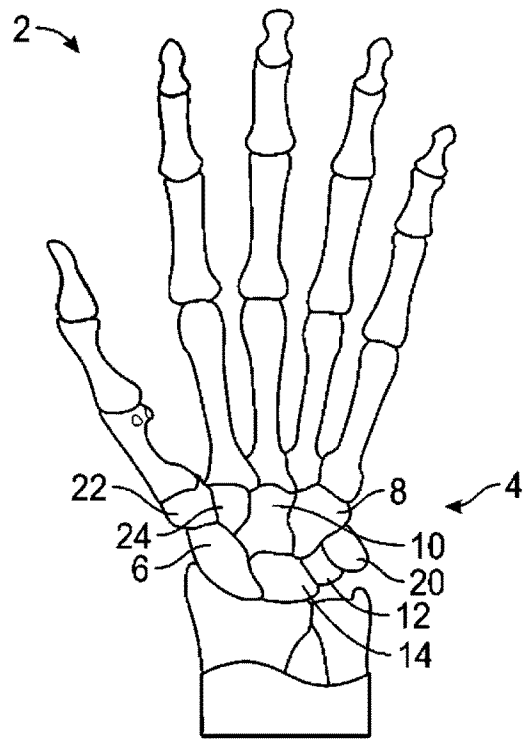
Figure 1B:
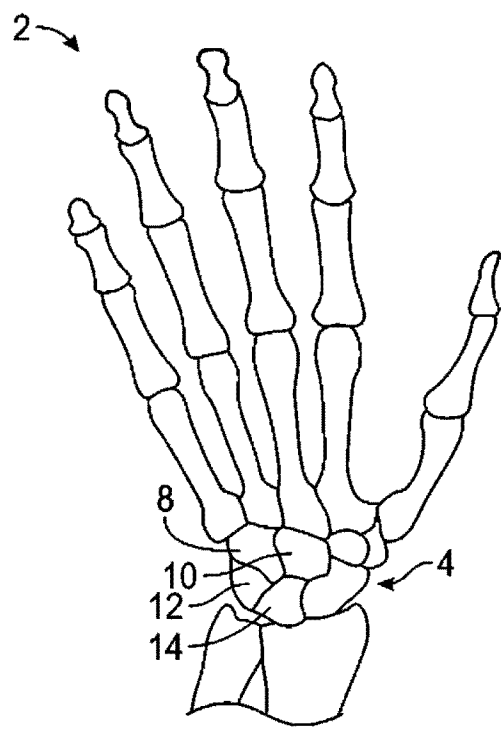
Figure 2:
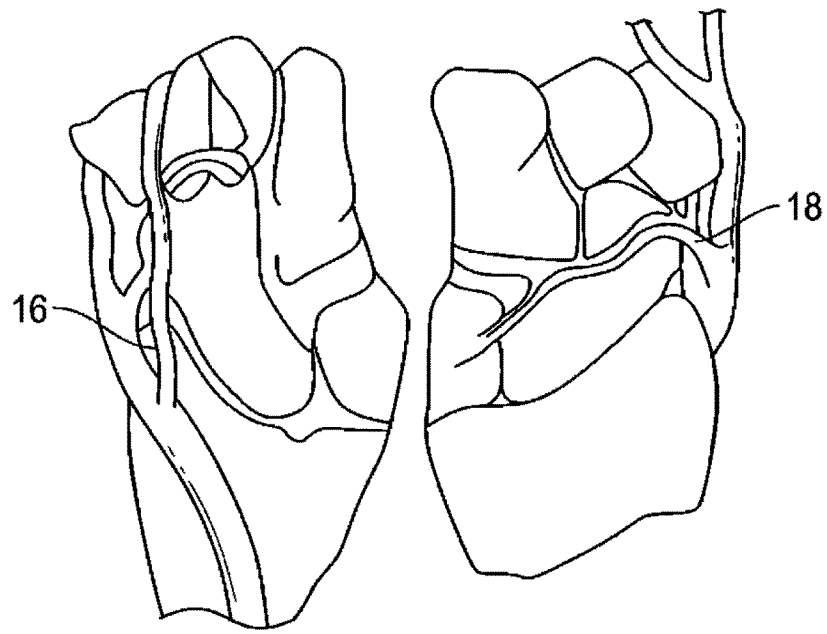
Figure 3:
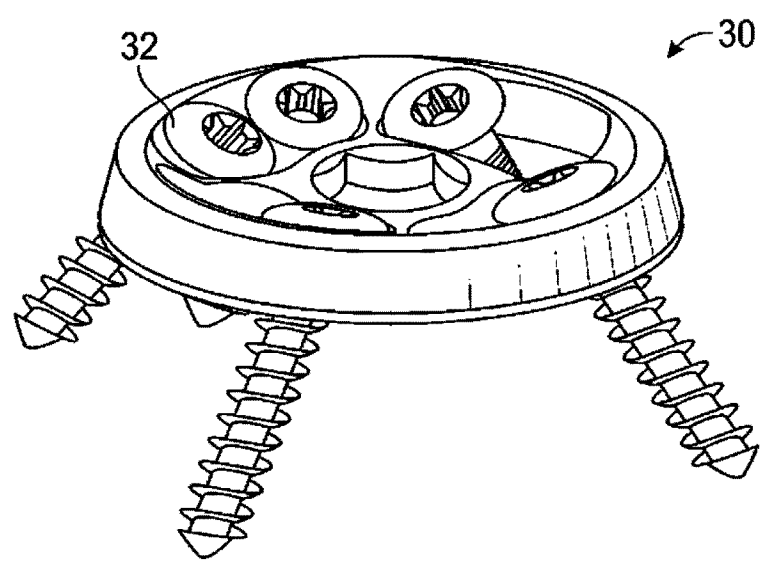
Figure 6:
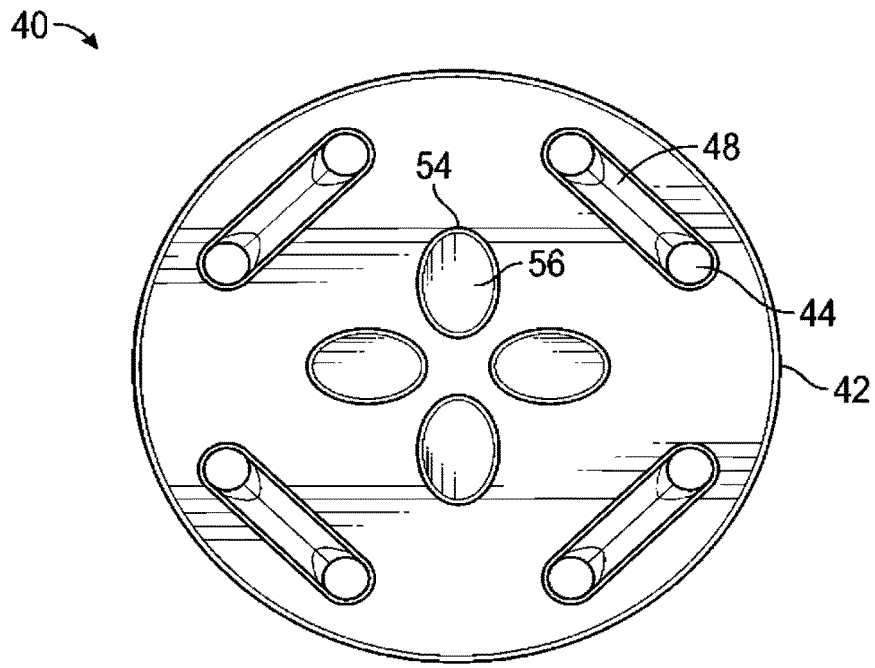
Figure 7:
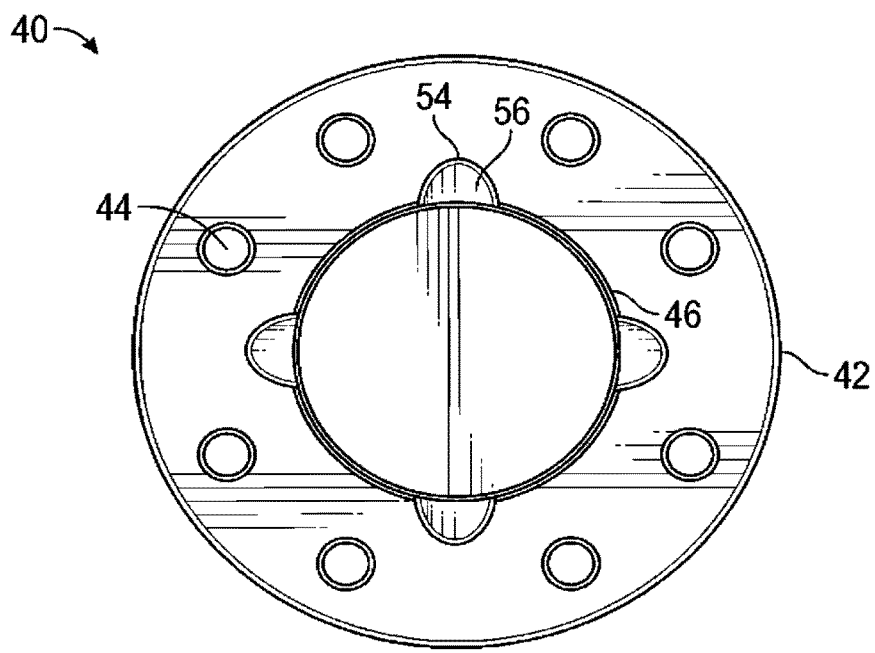

FIG. 4 is a top perspective schematic view of an exemplary orthopedic device of the present disclosure. FIG. 4A is a perspective schematic view of an exemplary fastener for the device. FIG. 5 is a side schematic view of the exemplary device shown in FIG. 4. FIG. 6 is a top schematic view of the exemplary device shown in FIG. 4. FIG. 7 is a bottom schematic view of the exemplary device shown in FIG. 4.

More specifically, the orthopedic device 40 is formed with a plate 42 having a first set of openings 44 located peripherally around the plate and formed through the plate. A downward extending cylinder 46 from the plate can be used to stabilize the plate to the bones during installation and for the bone stability for fusion after installation. The first set of openings 44 can be recessed in a channel 48, and the first set of openings can be disposed at distal portions of the channel. The first set of openings can be configured to accept a first set of fasteners 52, such as staples, through the plate for attachment to underlying bones. The staples can be preloaded to compress the bones into each other. The plate 42 can also be formed with a second set of openings 54 located centrally on the plate, the openings having threads 56 and formed through the plate at one or more orthogonal angles to a longitudinal axis 58 of the plate. A second set of fasteners 60, such as screws, can be inserted through the second set of openings 54 at the angle to help pull the bones into compression with each other. These fasteners 60 can be formed with a first coupling end 62 (proximal end) configured to couple to the plate, and a second coupling end 64 (distal end) configured to couple to the bones, where the first end and second end have different threads, including "compression screws." For example, a known compression screw is a "Herbert screw." The device can use a plurality of Herbert screws, which provide additional compression of bone against the device stem. These screws can be inserted from the center of the circular plate diagonally into the four carpal bones being fixated. The Herbert screws contain different pitches (thread counts) on the proximal and distal ends, so turning the screw will draw the bone in tight to the device and produce a slight compression for better fixation.

The device pulls radially inward the various bones to provide compression between the bones and create a condition to help the intended fusion. The first set of fasteners and the second set of fasteners can together couple to each bone with at least two and advantageously three fixations points of coupling to reduce multiple degrees of freedom.

The device is biocompatible, resistant to corrosion, and sufficient in mechanical strength. Bone motion restriction and inter-bone contact are significant factors to consider as they are directly correlated to the healing of the bone. Insufficient or inappropriate bone contact can cause failure to the bone healing. Conversely, the size of the device is not as important but is a consideration. The smaller the device is, the less chance there seems for it to cause damage by protruding or rubbing against the body. However, the size of the device has little correlation to the fusion process of the bones. Because of this, a smaller device is preferred, but as long as the device works, a larger size is accommodated. As a non-limiting example for illustrative purposes, the top plate of the device can generally be 20 mm in diameter or smaller, as limited by practical utility as would be known to those with ordinary skill in the art, to fit in most hands although the size can vary with the person and structure. Further, the total depth of device can generally be 10 mm or less, again as practically limited for the purpose, to fit in most hands although the size can vary with the person and structure.

Other exemplary, non-limiting design criteria include the sizing of the fasteners 60, such as screws, for the openings 54 that are centrally located in the (top) plate 42 and their interaction with the plate. For example, the value: d_screw is taken to be the maximum diameter of the screw, specifically the diameter of the threading. Treating the diameter of the screw in this manner allows calculations to be done to lessen clipping of the screws' threading. Additionally, in calculations, d_screw can be replaced with the value: D_screw, where D_screw=d_screw+C and C is some small constant to give a small safety margin for the screws.

$$h\_top \geq d\_screw \sin(45°) \qquad 1.$$

At a 45° entry angle for the screw (although other angles are possible including any angle between 15°-75° degrees or more), this height of the plate 42 was chosen to allow the threads at the head of the screw, that is, the first coupling end 62, additional metal to grip so that they do not grip the bone.

$$r\_base \geq (2h)\_top$$

$$d\_base(4h)\_top \qquad 2.$$

These values were chosen to reduce clipping of the threads from the screw on the opposite side of the device. These minimum values account for only the screws directly opposite one another, and this is just an assumption. In reality, the screws will be more likely to clip the screws set at 90° from them, and the geometries to take into account are ellipses with radii equal to d_screw and d_screw sin(45°)

$$1\ cm \geq h\_b \geq (2h)\_t \qquad 3.$$

In order to provide the bones a supporting surface for compression, these values were chosen. This allows the screw thread to be in the metal of the device as well as giving a minimum amount of metal against which the bones can be compressed.

$$1\ cm \geq r\_top \geq d\_screw + h\_top + r\_base$$

$$2\ cm \geq d\_top \geq 2(d\_screw + h\_top + r\_base) \qquad 4.$$

These values represent the exemplary values for the plate 42 so that both of the fasteners 52 and 60 will have grip on the device 2. These values assume the fasteners outer diameters to be touching at the outermost point.

The values in this example are given as examples and variations are possible, including and without limitation a variation of 10% plus or minus. The numerical parameters referenced in this application are approximations that may vary depending upon the desired properties sought to be obtained by the exemplary embodiments described herein.

Regarding material, in at least one embodiment, the device is an FDA Class II approved device. FDA Class II approved devices should be biocompatible, resistant to corrosion, and sufficient in mechanical strength. The inserted material should be able to protect the surrounding area from infection, migration, growth disturbance, or any sort of adverse reaction. Constantly being in contact with bodily fluids can often cause fracture from corrosion. Regarding the mechanical strength, advantageously, the material is sufficient in various properties that are common to the daily use of the wrist and hand. According to a study, unless fully absorbed, materials implanted into the body should stay intact for a minimum of 20 years for young individuals, and 15 years for older individuals.

For proper healing of the bones, a factor in material selection using polymers is that absorption within the body is not too rapid or too slow. Too fast does not provide sufficient time for healing and too slow can cause late reactions in the body even after sufficient healing. Common polymers used in scaphoid surgery are PGA (polyglycolic acid), PLA (polylactic acid), and PDS (polydioxanone). However, this material is somewhat weak in mechanical strength, but can be enhanced with self-reinforcing techniques. Self-reinforcement pins may have the initial bending strength up to 400 MPa, which corresponds to that of stainless steel.

Although these polymers showed promise, their strength may not be ideal to withstand the forces acting within the wrist. Therefore, non-absorbing materials can be used. For example, titanium and stainless steels are also options. Titanium Ti-6Al-4V and stainless steel grade 304 are popular in the medical field and pose little to no known problems when implanted into the body. Titanium especially has benefits such as a high strength to weight ratio, non-ferromagnetism, and its ability to resist corrosion.

An exemplary non-limiting installation procedure is outlined below:

The dorsal side of wrist is opened up and prepared for surgery.
The four carpals are brought together using K-wires.
A hole the diameter of the base of the device is drilled.
A hole the diameter of the top is drilled to countersink the device into the bone.
A plurality of staples, such as four (4) staples, are installed, such as by hammering, into the slots around the periphery of the device. These staples can be preloaded to compress the bones into each other.
A plurality of openings are drilled from holes in the center of the device into the bones.
A plurality of compression screws, such as four (4) screws, are installed into the bones and to pull the bones inward and increase compression between the bones.
The combination of the staples and compression screws couple to each bone with at least three fixations points of coupling to reduce multiple degrees of freedom
The incision can be closed.

Other and further embodiments utilizing one or more aspects of the inventions described above can be devised without departing from the disclosed invention as defined in the claims. For example, various shapes of the device, fasteners used with the device, sizes, materials, angles, clips, along with other variations can occur in keeping within the scope of the claims, and other variations.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalents of the following claims.

REFERENCES INCORPORATED BY REFERENCE HEREIN http://www.micromed.com/media/bilder/Sliding_platte_four-corner_fusion.jpg
http://morphopedics.wdfiles.com/local--files/scaphoid-fractures/BloodSupply.jpg
http://www.micromed.com/media/bilder/Sliding_platte_four-corner_fusion.jpg
http://clinicalgate.com/wp-content/uploads/2015/03/B9781416040835000512_f049002ab-97814160-40835.jpg
https://www.researchgate.net/profile/George_Kontakis/publication/6317814_Bioabsorbable_materials_in_orthopaedics/links/00b7d52017037c-da8f000000.pdf
https://www.researchgate.net/profile/George_Kontakis/publication/6317814_Bioabsorbable_materials_in_orthopaedics/links/00b7d52017037-cda8f000000.pdf
A. D. Duckworth, P. J. Jenkins, S. A. Aitken, N. D. Clement, C. M. Court-Brown, and M. M. McQueen, "Scaphoid fracture epidemiology," Wolters Kluwer, February 2012. [Online]. Available: http://journals.Iww.com/jtrauma/abstract/2012/02000/scaphoid_fracture_epidemiology. 46.aspx?trendmd-shared=0. [Accessed: 3 Nov. 2016].
I. L. Trail, "The long-term outcome of four-corner fusion," National Center for Biotechnology Information, 4 May 2015. [Online]. Available: https://www.ncbi.nlm.nih.gov/pubmed/25945298. [Accessed: 3 Nov. 2016].
G. M. Kontakis, J. E. Pagakalos, T. I Tosounidis, J. Melissas, P. Katonis, "Bioabsorbable materials in orthopaedics," May 2007. [Online]. Available: https://www.researchgate.net/profile/George_Kontakis/publication/6317814_Bioabsorbable_materials_in_orthopaedics/links/00b7d52017037cda8f000000.pdf
E. Waris, N. Ashammakhi, O. Kaarela, T. Raatikainen, J. Vasenius, "Use of Bioabsorable Osteofixation Devices in the Hand," December 2004. [Online]. Available: http://www.sciencedirect.com/science/article/pii/S0266768104000415

What is claimed is:

1. An orthopedic device for coupling a plurality of bones, comprising:
    a plate formed with a first set of openings located peripherally around the plate being closer to a periphery of the plate than a center of the plate and formed through the plate and a second set of openings located centrally on the plate being closer to a center of the plate than the periphery of the plate and formed through the plate at an angle to a longitudinal axis of the plate, the angle being configured to allow a plurality of second fasteners inserted in the second set of openings and coupled to the bones to pull radially inward the bones to provide compression between the bones.

2. The device of claim 1, wherein the first set of openings comprises at least two openings recessed in a lateral channel formed on the plate, the at least two openings being formed through the plate at distal portions of the channel.

3. The device of claim 1, wherein the first set of openings is configured to accept a plurality of first fasteners through the plate to couple underlying bones to the plate.

4. The device of claim 3, wherein the first fasteners comprise staples.

5. The device of claim 1, wherein the second set of openings are configured to allow the second fasteners to be inserted through the plate and couple underlying bones to the plate.

6. The device of claim 1, wherein one or more of the second fasteners comprises a first coupling end configured to couple to the plate, and a second coupling end configured to couple to the bones, the first end and second end having different pitch threads.

7. The device of claim 1, wherein the angle of the second set of openings is directed away from the longitudinal axis of the plate.

8. A method of coupling an orthopedic device to a plurality of bones, the device having a plate formed with a first set of openings located peripherally around the plate being closer to a periphery of the plate than a center of the plate and formed through the plate and a second set of a plurality of openings located centrally on the plate being closer to a center of the plate than the periphery of the plate and formed through the plate at an angle to a longitudinal axis of the plate, the method comprising:
    locating the plate adjacent the bones;
    forming holes in the bones;
    inserting a first set of fasteners through the peripherally located openings and into the bones;
    inserting a second set of fasteners through the centrally located openings and into the bones;
    pulling the bones toward a longitudinal axis of the plate; and
    at least partially securing the bones toward a longitudinal axis of the plate with the second set of fasteners.

9. The method of claim 8, further comprising at least partially stabilizing the bones with the first set of fasteners.

10. The method of claim 9, further comprising installing the first set of fasteners into the bones prior to inserting the second fasteners into the bones.

11. The method of claim 8, further comprising preloading the first set of fasteners to compress the bones into each other.

12. The method of claim 8, wherein the first set of fasteners comprise staples and comprising inserting the staples through the peripherally located openings.

13. The method of claim 8, wherein the first set of fasteners and the second set of fasteners couple to each bone with at least three fixations points of coupling defining a plane to reduce multiple degrees of freedom.

* * * * *

UNITED STATES PATENT AND TRADEMARK OFFICE
CERTIFICATE OF CORRECTION

PATENT NO. : 11,141,285 B2
APPLICATION NO. : 16/055899
DATED : October 12, 2021
INVENTOR(S) : Fisher et al.

It is certified that error appears in the above-identified patent and that said Letters Patent is hereby corrected as shown below:

On the Title Page

Delete the title page and substitute therefore with the attached title page consisting of the corrected illustrative figure(s).

In the Drawings

Please replace FIGS. 1A-7 with FIGS. 1A-7 as shown on the attached pages.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

(12) United States Patent
Fisher et al.

(10) Patent No.: US 11,141,285 B2
(45) Date of Patent: Oct. 12, 2021

(54) CARPAL BONE FUSION DEVICE AND METHOD

(71) Applicant: BAYLOR UNIVERSITY, Waco, TX (US)

(72) Inventors: Connor Fisher, New Braunfels, TX (US); Zachary Collins, Colorado Springs, CO (US); Alex Chen, Frisco, TX (US); Chad Regensberg, Apple Valley, CA (US); Tim Adeleye, The Woodlands, TX (US); Joshua Buckner, Dedham, MA (US)

(73) Assignee: Baylor University, Waco, TX (US)

( * ) Notice: Subject to any disclaimer, the term of this patent is extended or adjusted under 35 U.S.C. 154(b) by 0 days.

(21) Appl. No.: 16/055,899

(22) Filed: Aug. 6, 2018

(65) Prior Publication Data
US 2020/0038195 A1   Feb. 6, 2020

(51) Int. Cl.
A61F 2/42 (2006.01)
A61B 17/064 (2006.01)
A61B 17/80 (2006.01)
A61F 2/30 (2006.01)

(52) U.S. Cl.
CPC ........ *A61F 2/4261* (2013.01); *A61B 17/0642* (2013.01); *A61B 17/8014* (2013.01); *A61B 17/8057* (2013.01); *A61B 17/8061* (2013.01); *A61F 2/30749* (2013.01); *A61F 2002/30622* (2013.01); *A61F 2002/4271* (2013.01)

(58) Field of Classification Search
CPC .... A61F 2/4261; A61F 2/4264; A61F 2/4266; A61F 2/4269; A61B 17/0642; A61B 2017/0645; A61B 17/8061
See application file for complete search history.

(56) References Cited

U.S. PATENT DOCUMENTS 5,201,737 A * 4/1993 Leibinger ............ A61B 17/688
606/280
5,511,565 A * 4/1996 Syers ................. A61B 17/8071
128/859
5,578,036 A * 11/1996 Stone ................. A61B 17/688
606/281
(Continued)

FOREIGN PATENT DOCUMENTS

WO    2013036362 A1    3/2013

OTHER PUBLICATIONS

Kontakis, G. M., Pagkalos, J. E., Tosounidis, T. I., Melissas, J., Katonis, P., "Bioabsorable materials in orthopaedics", Acta Orthopaedica Belgica, May 2007, pp. 159-169, vol. 73.
(Continued)

*Primary Examiner* — Matthew J Lawson
(74) *Attorney, Agent, or Firm* — Jackson Walker, LLP

(57) ABSTRACT

The present disclosure provides an orthopedic device and method for carpal fusion that provides bone to bone compression and multiple fixation points to decrease multiple degrees of freedom and motion of carpal bones. The device is biocompatible, resistant to corrosion, and sufficient in mechanical strength. Bone to bone compression and fixation points can be increased by using a first set of fasteners in a peripheral portion of the device to couple through the device into bone structure, and a second set of fasteners in a central portion of the device can be coupled through the device into the bone structure.

13 Claims, 4 Drawing Sheets

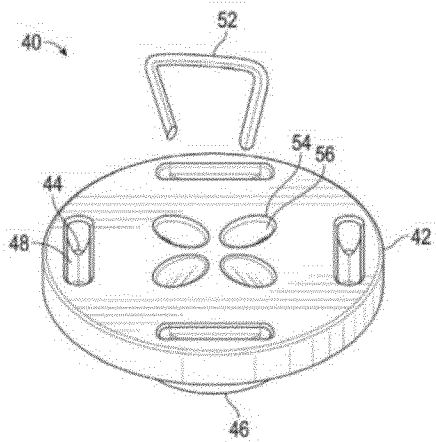

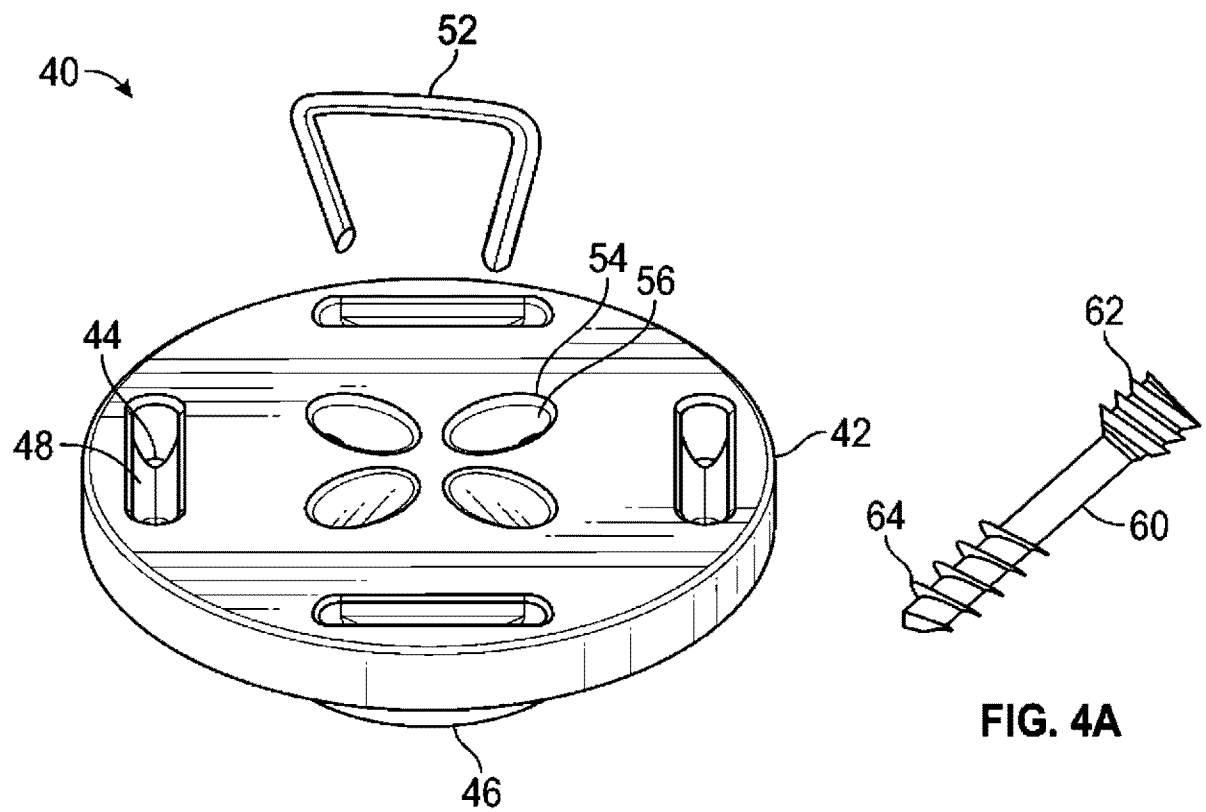
FIG. 4
FIG. 4A
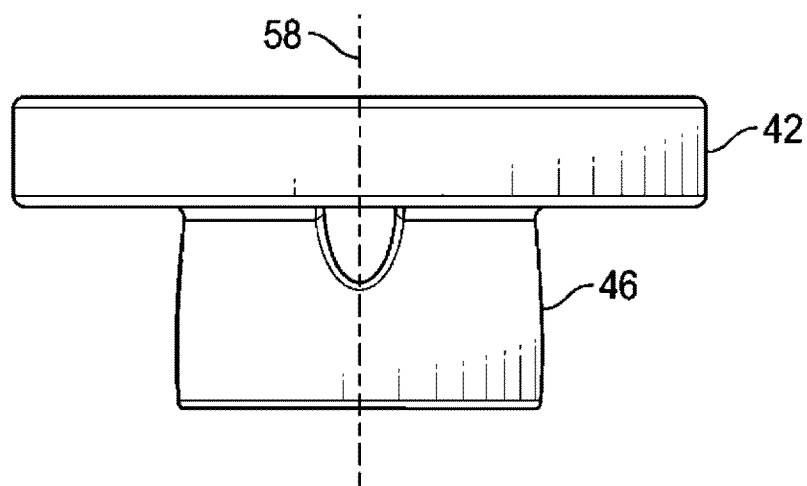
FIG. 5